United States Patent [19]
Fehr et al.

[11] Patent Number: 5,850,030
[45] Date of Patent: Dec. 15, 1998

[54] REDUCED LINOLENIC ACID PRODUCTION IN SOYBEANS

[75] Inventors: Walter R. Fehr; Earl G. Hammond, both of Ames, Iowa

[73] Assignee: Iowa State University Research Foundation, Inc., Ames, Iowa

[21] Appl. No.: 772,470

[22] Filed: Dec. 23, 1996

[51] Int. Cl.$^6$ ............................... A01H 5/00; A01H 5/10; A01H 1/02; C12N 5/04

[52] U.S. Cl. .......................... 800/312; 800/264; 435/415; 435/426; 435/430

[58] Field of Search .................................... 800/200, 255, 800/DIG. 26, DIG. 69; 435/415, 426, 430; 47/58, DIG. 1; 426/601

[56] References Cited

U.S. PATENT DOCUMENTS

| | | | |
|---|---|---|---|
| 4,948,811 | 8/1990 | Spinner et al. | 514/560 |
| 5,530,183 | 6/1996 | Fehr et al. | 800/200 |
| 5,534,425 | 7/1996 | Fehr et al. | 435/172.1 |

OTHER PUBLICATIONS

Rahman, "Inheritance of Reduced Linolenic Acid Content in Soybean", Theoretical and Applied Genetics, vol. 94, 1997, pp. 299–302, XP002061215.

Rennie et al., "New Allele at the FAN Locus in the Soybean Line A5", Crop Science, vol. 31, No. 2, 1991, pp. 297–301, XP002061216.

Nickell A D et al., "Genetic Relationships Between Loci Controlling Palmitic and Linolenic Acids in Soybean", Crop Science, vol. 31, No. 5, 1991, pp. 1169–1171, XP002048037.

Rennie, B., "Mapping a Second Fatty Acid Locus to Soybean Linkage Group 17", Crop Science, vol. 29, No. 4, 1989, pp. 1081–1083, XP002061217.

Rahman, S., "Low Linolenate Sources at the FAN Locus in Soybean Lines M–5 and IL–8", Breeding Science, vol. 46, No. 2, 1996, pp. 155–158, XP002061218.

"The Flavor Problem of Soybean Oil. VIII Linolenic Acid", H.J. Dutton et al., *The Journal of the American Oil Chemists' Society*, vol. 28, pp. 115–118, (Mar. 1951).

"The Study of 20 Varieties of Soybeans With Respect to Quantity and Quality of Oil, Isolated Protein, and Nutritional Value of the Meal", O.H. Alderks, *The Journal of the American Oil Chemists' Society*, vol. 26, pp. 126–132, (Mar. 1949).

"Regulation of Linolenic Acid in Soybeans and Gene Transfer to High Yielding, High Protein Germplasm", *In Proceedings World Conference on Emerging Technology in Fat & Oil Industry*, R.F. Wilson et al., AOCS Publisher, Baldwin (editor), pp. 386–391.

"Physiological Factors Affecting Composition of Soybeans. I. Correlation of Temperatures During Certain Portions of the Pod Filling Stage with Oil Percentage in Mature Beans", Robert W. Howell et al., *Agronomy Journal*, vol. 45, pp. 526–528, (1953).

"Soybean Germplasm Evaluation—Search for Lowlinolenic Lines", Robert Kleiman and James F. Cavins, *The Journal of the American Oil Chemists' Society*, vol. 59, No. 4, p. 305A, (Apr. 1982).

"Note on the Quality Constituents of Soybean (*Glycine Max* (L) *Merril*) Varieties", R.D. Tripathi et al., *Indian J. Agric. Res.*, 1975, vol. 9, No. 4, pp. 220–222.

"The Linolenic Oils", A.E. Bailey, *Industrial Oils and Fats Products*, 1945 edition, p. 173.

"Occurrence and Inheritance of Linolenic and Linoleic Acid in Soybean Plants", H.B. White, Quakenbush and Probst., *The Journal of the American Oil Chemists' Society*, vol. 38, pp. 113 to 117, (Mar. 1961).

"Oil Quality Improvement in Soybeans–*Glycine max* (L) *Merr.*", *Sonderdruck aus fette*, by E.G. Hammond and Walter R. Fehr, Seifen, Anstrichmittel 77, pp. 97–101 (1975).

"Progress in the Selection for Altered Fatty Acid Composition in Soybeans", Richard F. Wilson et al., *Crop Science*, vol. 21, Sep.–Oct. 1981, pp. 788–791.

"Genetic Alteration of Soybean Oil Composition by a Chemical Mutagen", J.R. Wilcox et al., *The Journal of the American Oil Chemists Society*, vol. 61, No. 1, (Jan. 1984), pp. 97–100.

"Composition of a Soybean Oil Of Abnormally Low Iodine Number", F.G. Dollear et al., *Oil & Soap*, vol. 15, pp. 263–264, (Oct. 1938).

"Fatty Acid Composition of Oil From Soybean Seeds Grown at Extreme Temperatures", B.D. Rennie et al., *The Journal of the American Oil Chemists Society*, vol. 66, pp. 1622–1624, (Nov. 1989).

*Primary Examiner*—Elizabeth F. McElwain
*Attorney, Agent, or Firm*—Burns, Doane, Swecker & Mathis, L.L.P.

[57] ABSTRACT

Soybeans (i.e., Glycine max L. Merr.) possessing a novel genetic determinant for the reduced production of linolenic acid in the endogenously formed vegetable oil of the seeds are provided. Such genetic determinant is the homozygous recessive fan3fan3 gene pair that has been found to be capable of formation through mutagenesis. Once formed, such genetic determinant can be readily transferred to other soybean lines and cultivars where it is similarly expressed on a reliable basis under conventional field growing conditions. In a preferred embodiment a soybean plant possesses the combined presence of the homozygous recessive gene pairs (1) fan1fan1 or fan1(A5)fan1(A5), (2) fan2fan2, as well as (3) fan3fan3 for reduced linolenic acid formation in the seeds and has been found that an unusually low expression for linolenic acid production in the resulting vegetable oil of the seeds is provided that is less than 1.3 percent by weight and most preferably is no more than 1.1 percent by weight based on the total fatty acid content. A vegetable oil is made possible in this instance that is particularly well suited for frying applications in the absence of the need for hydrogenation.

4 Claims, No Drawings

REDUCED LINOLENIC ACID PRODUCTION IN SOYBEANS

BACKGROUND OF THE INVENTION

Soybean (i.e., Glycine max L. Merr.) seeds are recognized to represent one of the most important oilseed crops presently being grown in the world. Such seeds provide an excellent source of vegetable oil as well as a source of protein that can serve as an alternative to animal meat products. For instance, tofu and soymilk derived from soybean seeds provide a major source of protein for the people of China and Southeast Asia.

While soybean oil represents an important worldwide food source, flavor and stability problems associated with its customary fatty acid composition may reduce its attractiveness in some applications. Soybean oil contains five different fatty acids as its major components. These five fatty acids are: palmitic acid (16:0) which averages about 11 percent by weight, stearic acid (18:0) which averages about 4 percent by weight, oleic acid (18:1) which averages about 20 percent by weight, linoleic acid (18:2) which averages about 57 percent by weight, and linolenic acid (18:3) which averages about 8 percent by weight of the total fatty acids. The stability problem which influences the flavor of soybean oil has been attributed to the oxidation of its fatty acids, and particularly to the oxidation of the linolenic acid (C18:3) component.

The unsaturated fatty acids in soybean oil are known to be susceptible to oxidation; and the polyunsaturated fatty acids, linoleic and linolenic, are recognized to oxidize more rapidly than the oleic acid component. The oxidized fatty acids apparently decompose to form volatile flavor-imparting compounds, to at least some degree. It is not clear why linolenic acid contributes so significantly to the flavor and stability of oils; however, based upon experiments using blends of oils having different percentages of linolenic acid, all oils containing more than about 1% linolenic acid or so appear to share this property to some extent. For more than 45 years, the flavor and stability characteristics of soybean oil have been attributed to the high linolenic acid level of the soybean oil (Dutton et al., *J. Am. Oil Chem. Soc.,* 28:115, 1951).

To attempt to obviate the flavor and stability problems of soybean oil due to the linolenic acid content, various approaches have been proposed. Such processing of the soybean vegetable oil includes (1) minimizing the ability of the fatty acids to undergo oxidation by adding metal chelating agents or packaging in the absence of oxygen, or (2) the elimination of the endogenous linolenic acid by selective hydrogenation. These approaches have not been entirely satisfactory. Such additional processing is expensive, time consuming, commonly is found not to be completely effective, and frequently is found to generate undesirable byproducts. Thus, while selective hydrogenation to reduce the linolenic acid content may improve oil stability somewhat, this also generates positional and geometric isomers of the unsaturated fatty acids that are not present in the natural endogenously formed soybean oil.

The inability to solve the stability and flavor problem adequately, together with the undesirable aspects of the necessary processing technology, reduces the end uses for soybeans to some degree, especially where such after processing of the endogenously formed oil is either unavailable or is economically inappropriate or where consumer attitudes discourage the use of hydrogenation.

Primarily because of the limitations of such after processing technology and because of the worldwide significance of soybean oil as a food source, considerable effort has been expended over many years to attempt to understand the genetic mechanism which controls the linolenic acid level in soybeans. Indeed, studies on this subject date back to at least 1949. According to Howell et al., as many as five different genes were thought to possibly control the linolenic acid level in soybeans (*J. Am. Oil Chem. Soc.,* 26:126, 1949). Investigations into the biochemical mechanism suggest that linolenic acid (C18:3) results from successive desaturations of first oleic acid (C 18:1) and second linoleic acid (C18:2). Thus, genes controlling at least two different desaturase systems may be involved. To date, the genes which can control the linolenic acid level of soybeans have not been fully identified, and the biochemical pathways that are involved have not been fully elucidated.

Even the mode of inheritance of linolenic acid production in soybeans sometimes is unclear because various studies over the years have presented conflicting results. For example, early investigation suggested that the linolenic acid content in soybeans was maternally controlled. A later study suggested the mechanism of inheritance was even more complicated, being partially maternally and partially embryonically controlled (Wilson et al., "Regulation of Linolenic Acid in Soybeans and Gene Transfer of High Yielding, High Protein Germplasm", R. A. Baldwin (Ed.), Proceedings of the World Conference on Emerging Technologies in the Fats and Oils Industry, Am. Oil Chem. Soc., Champaign, Ill., (1986). The Wilson et al. study thus reports that the genes which regulate oleic acid desaturation are controlled by the maternal parent, while the genes which control linoleic acid desaturation are governed by the embryonic genotype.

Complications also have arisen because it has been long recognized that the linolenic acid content of soybeans sometimes can be influenced by the environment in which the seeds are grown (Howell et al., *Agron. J.,* 45:526, 1953). Such environmental factors are said to include temperature, photoperiod (i.e., day length), the geographical location, and the planting date.

In summary, despite the substantial effort over the years, the genetic mechanism for controlling the linolenic acid content in soybean vegetable oils is not fully understood. Genetic research to provide soybeans characterized by reduced levels of linolenic acid is thus quite complex. There is little to guide efforts of this sort on a reliable basis. Research efforts accordingly have been largely empirical with no assurance of success.

However, despite the relative lack of understanding of the genetic mechanism which controls the level of linolenic acid content in soybeans, substantial work over the years has been carried out to attempt to isolate soybean lines having low levels of endogenously formed linolenic acid, as well as to attempt to use genetic manipulation to develop soybean lines characterized by low levels of linolenic acid. The lowest level of linolenic acid in the oil of natural soybean germplasm accessions was found by some researchers to be 4.2 percent by weight (Kleinman and Cavins, *J. Am. Oil Chem. Soc.,* 59:305A, 1982).

Tripathi et al., *Indian J. Agric. Res.,* 1975, 9(4):220–222, "Note On The Quality Constituents Of Soybean (Glycine Max (L) (Merrill) Varieties", did report, among other things, the fatty acid contents of what were stated to be twelve soybean varieties grown at the Oilseed Research Farm, Kalianpur, Kanpur, during kharif, 1970. While the linolenic acid contents reported vary from 0.0 to 5.3 percent by weight, such contents were calculated by the Scholfield and Bull formulae (Tripathi et al., referencing Bailey, 1945, *Industrial Oil and Fat Products,* Interscience Publishers, Inc., New York). In general, Scholfield and Bull's methodology predicted fatty acid composition from the iodine value. Their data points were scattered about these linear predictions, and for linolenic acid a standard error of 1.5 percent by weight was reported. Moreover their method was standardized on lines with typical soybean oil. There is no evidence that their formula is applicable to oils having atypical compositions produced by mutation. Indeed, it would be surprising if their formula was applicable to such samples. It should be noted also that the equation of Scholfield and Bull was based on the iodine-thiocyanogen method which is recognized to be subject to considerably more error than gas liquid chromatography when measuring fatty acid composition.

In the first place, the public availability of the twelve soybean varieties referenced by Tripathi et al. is uncertain. Applicants have made repeated attempts to obtain samples of such varieties and have not been successful in securing all of them.

Secondly, and importantly, what has been determined on the basis of samples provided is that there is no correlation between the linolenic acid values reported by Tripathi et al. and those determined by gas liquid chromatography. Gas liquid chromatography is recognized to be the current and most reliable analytical standard used for the fatty acid analysis of a vegetable oil. Set forth below, for all samples obtained, is a comparison of the linolenic acid values reported in Tripathi et al. with those obtained by gas liquid chromatography (GLC).

| Variety | Tripathi et al. Values (weight percent) | GLC Values (weight percent) | |
|---|---|---|---|
| | | Seed From U.S.[1] | Seed From India[2] |
| Bragg | 4.5 | 7.6 | 5.8 |
| Type 49 | 4.9 | — | 5.9 |
| Lee | 3.7 | 6.7 | 4.0 |
| Improved Pelican | 2.4 | 7.2 | 7.0 |
| Punjab-1 | 0.4 | 6.1 | 5.6 |
| IC2716 | 1.0 | — | 4.4 |
| Type 33 | 5.3 | — | — |
| Type 64 | 0.0 | — | — |
| Type 1 | 1.4 | — | — |
| IC217 | 2.8 | — | 5.9 |
| IC222 | 4.1 | — | — |
| IC213 | 4.2 | — | — |

[1]Seed produced in United States and obtained from USDA, Soybean Production Research, Stoneville, Mississippi.
[2]Seed obtained from the National Bureau of Plant Genetic Resources, New Delhi, India.

In summary, based upon what Applicants have found, there would be no sound basis for concluding that any of the varieties referenced by Tripathi et al. possessed extremely low linolenic acid contents when such contents are determined by gas liquid chromatography. Rather, these varieties appear to have rather typical to slightly reduced linolenic acid contents. These linolenic acid contents tend to be above the minimum later reported by Kleinman et al. for natural soybean germplasm accessions.

Hybridization work to reduce the linolenic acid of soybeans dates back at least as far as 1961. White et al. identified an $F_2$ plant obtained by hybridization with only 3.35 percent by weight linolenic acid (White, Quackenbush and Probst, "Occurrence and Inheritance of Linolenic and Linoleic Acid in Soybean Seeds", *J. Am. Chem. Soc.,* Vol. 38, pages 113 to 117, 1961). However, this level was not maintained in succeeding generations and accordingly there is no evidence of genetic control.

During 1975 the present Applicants utilized recurrent selection to produce soybean strains having levels of linolenic acid of about 5.5 percent by weight (Fette Seifen Anstrichin., 77:97 101, 1975). Wilson and Burton isolated two different lines, designated N78-2245 and P1123440. These lines were selected for their levels of oleic acid, linoleic acid and linolenic acid. From this experimentation, two genetic systems were discovered, one that primarily governs oleic acid desaturation and a second that acts genotypically upon linoleic acid desaturation. These two gene loci are said to determine the low linolenic acid content (*Crop Science,* 21:788, 1981).

Wilcox et al. treated soybeans with ethyl methane sulfonate (EMS) to produce a mutant designated C1640 (*J. Am. Oil Chem. Soc.,* 61:97, 1984). The level of linolenic acid averaged 3.4 percent by weight. It was stated that the linolenic acid trait could be transferred to other lines by backcrossing.

In our commonly assigned U.S. Pat. No. 5,534,425 soybeans are disclosed which form a reduced endogenous linolenic acid content. Also, in our commonly assigned U.S. Pat. No. 5,530,183, soybean variety 9253 is disclosed that provides a specialty oil having a reduced endogenous linolenic acid content.

F. G. Dollear et al. reported in *Oil & Soap,* 15:263–264, (1938) that soybean oil from the Dunfield cultivar grown at Columbia, Mo., U.S.A. in 1936 had a very low iodine value and by using the iodine and thiocyanogen values, they calculated a linolenate content of 2.9 percent. When grown at Lafayette, Ind., U.S.A. in 1937, the oil measured 6.0 percent linolenate. They attributed the low linolenate percentage to variation in growing conditions since 1936 set heat records. B. D. Rennie et al. in *J. Am. Oil Chem. Soc.,* 66:1622 (1989) stated that high temperatures can cause depression of the linolenate content. When the Dunfield cultivar was grown in Iowa, U.S.A., it did not exhibit an abnormally low linolenate content as determined by gas liquid chromatography.

Despite these efforts there has remained a need for soybeans having a still further genetically-controlled reduction of linolenic acid in the endogenously produced vegetable oil produced within the seeds.

It is an object of the present invention to provide under conventional field growing conditions soybean seeds possessing while under genetic control a reduced level of linolenic acid in the endogenously produced vegetable oil wherein the genetic control is attributable to a new allele.

It is an object of the present invention to provide soybean plants capable upon self-pollination of forming seeds that possess while under genetic control a reduced level of linolenic acid in the endogenously produced vegetable oil wherein the genetic control is attributable to a new allele.

It is an object of the present invention to provide a vegetable oil derived from soybeans following crushing and extraction that exhibits while under genetic control (as described) a further reduced concentration of linolenic acid wherein the level of linolenic acid is less than that previously available in an endogenously formed soybean seed oil.

It is another object of the present invention to provide in soybeans a novel heretofore unknown homozygous recessive fan3fan3 gene pair that is capable of reducing linolenic acid production in the endogenously produced vegetable oil present in the seeds.

It is another object of the present invention to combine the homozygous recessive gene pairs (1) fan1fan1 or fan1(A5)

fan1(A5), (2) fan2fan2, (3) fan3fan3 in a single soybean plant which in combination have been found to make possible the expression, while under genetic control, of a lesser concentration of linolenic acid in the endogenously formed vegetable oil formed in the soybean seeds of such plant than has heretofore been possible.

It is a further object of the present invention to provide a vegetable oil derived from soybean seeds that contains a reduced endogenously produced linolenic acid content while under genetic control which is particularly suited for uses requiring enhanced resistance to the development of oxidized flavors, such as products requiring a long shelf-life, or which are routinely subjected to rigorous conditions during use including cooking or frying oils.

These and other objects, as well as the scope, nature, and utilization of the claimed invention will be apparent to those skilled in the art from the following detailed description and appended claims.

SUMMARY OF THE INVENTION

Soybean seeds and soybean plants are provided possessing the homozygous recessive gene pair fan3fan3 for the expression of a reduced linolenic acid content in the endogenously formed vegetable oil of the seeds. Such fan3fan3 gene pair is present in A26 having ATCC Accession No. 97812 and can be readily transferred to other soybean plants.

Soybean seeds and soybean plants are provided that exhibit a reduced linolenic acid content in the endogenously formed vegetable oil of the seeds wherein the linolenic acid content is attributable to the combined presence of the homozygous recessive gene pairs (1) fan1fan1 or fan1(A5)fan1(A5), (2) fan2fan2, and (3) fan3fan3, or a soybean seed descended therefrom that possesses the homozygous recessive gene pairs. The recessive gene pairs fan1(A5)fan1(A5), fan2fan2, and fan3fan3 in combination are present in A29 having ATCC Accession No. 97813.

A vegetable oil also is provided possessing a reduced linolenic acid content following removal from a soybean seed wherein the linolenic acid concentration is attributable to the combined presence of the homozygous recessive gene pairs (1) fan1fan1 or fan1(A5)fan1(A5), (2) fan2fan2, and (3) fan3fan3. In a preferred embodiment, the linolenic acid content of the vegetable oil is attributable to the combined presence of the gene pairs (1) fan1(A5)fan1(A5), (2) fan2fan2, and (3) fan3fan3.

DESCRIPTION OF PREFERRED EMBODIMENTS

Available soybean varieties typically grown commercially for vegetable oil production in the United States commonly form oils within the resulting soybean seeds under conventional field growing conditions that contain on the order of 8 percent by weight linolenic acid based upon the total fatty acid content. Soybean variety 9253 that also is available commercially commonly forms linolenic acid in the endogenous vegetable oil in a concentration of approximately 2.5 to 3.5 percent by weight based upon the total fatty acid content. Such soybean variety is described in U.S. Pat. No. 5,530,183. However, a need has remained for additional soybean plant material that is capable of yielding reduced levels of linolenic acid in the vegetable oil of the seeds while under genetic control.

It now has been found through empirical research that it is possible to form through mutagenesis soybean plants possessing the novel homozygous recessive gene pair fan3fan3 for the expression of a reduced linolenic acid content in the endogenously formed vegetable oil of the seeds.

During the formation of the subject fan3fan3 gene pair, a conventional soybean line or cultivar preferably having superior agronomic characteristics for growing at a preselected locale is subjected to such mutagenesis, and selection for the fan3fan3 gene pair is carried out in subsequent generations while observing the plant phenotype for reduced linolenic acid content and conducting inheritance studies in order to ascertain and confirm the different locus for the responsible fan3fan3 gene pair. The ability to form the requisite fan3fan3 gene pair via mutagenesis is not believed to require the selection of a specific soybean starting material.

Plant cells capable of regeneration (e.g., seeds, microspores, ovules, pollen, vegetative parts) of Glycine max L. Merr. are subjected to a mutagenesis treatment during at least one generation, a soybean plant is regenerated from the cells to form soybean seeds in at least one subsequent generation, and selections initially are made on the basis of reduced linolenic acid in the endogenously formed vegetable oil of such seeds. The mutagenesis preferably is carried out under conditions wherein the plant cells are in the form of a soybean seed. Good results have been obtained through the use of a chemical mutagen that heretofore has been recognized to be capable of creating substantial genetic variation in plant material. In a preferred embodiment, ethyl methanesulfonate (EMS) is utilized as the chemical mutagen. Other representative chemical mutagens include N-nitroso-N-methylurea (NMU), sodium azide, 1-methyl-3-nitro-1-nitrosoquanidine (nitrosoquanidine), etc.

In a preferred embodiment wherein seeds are treated, the mutagen concentration and exposure time are selected so as to produce a survival rate in the resulting seeds of approximately fifty percent. Typically approximately 1 ml. of the mutagen solution is provided per seed and the seeds are soaked for several hours while aerating the solution. The seeds next are removed, rinsed with water, and are planted while wet in the field where they are immediately watered.

It has been found that the presence of the fan3fan3 gene pair in an otherwise conventional soybean variety commonly has the ability to alter the phenotype so that the linolenic acid content of the endogenously formed vegetable oil is reduced by approximately 1.5 to 5 percent by weight based upon the total fatty acid content as determined by gas liquid chromatography. The level of expression of the fan3fan3 gene pair with respect to linolenic acid production in an otherwise conventional soybean variety has been found to be considerably influenced by the environmental conditions that are encountered with higher temperatures commonly leading to a greater reduction in linolenic acid production within the specified range.

Such fan3fan3 gene pair must be provided in the homozygous recessive form in order to express such reduced linolenic acid content. It further has been demonstrated through inheritance studies that such fan3fan3 gene pair is present at a different locus than previously reported genes for the reduction of linolenic acid content, such as fan1fan1, fan1(A5)fan1(A5), and fan2fan2. For instance, when a plant possessing the fan3fan3 gene pair is crossed with plants possessing such other gene pairs for reduced linolenic acid content, none of the $F_1$ progeny will exhibit the desired level of reduced linolenic acid content in the endogenously produced vegetable oil of the resulting plants and segregation for such desired reduced linolenic acid trait will be manifest in subsequent generations following self-pollination of the resulting $F_1$ progeny as the components of the requisite fan3fan3 gene pair are provided an opportunity to recombine. Also, the presence of such fan3fan3 gene pair in a given soybean plant can be confirmed by crossing such plant with A26 (described hereafter) that is known to possess such homozygous recessive gene pair and observing the phenotype for reduced linolenic acid content in subsequent generations while confirming the mode of inheritance for such trait. When the fan3fan3 gene pair is present in a given plant and is crossed with A26 or other confirmed source for the requisite gene pair, all offspring will express the reduced linolenic acid content in the next generation in the absence of segregation.

It further has been found when grown under conventional field growing conditions that the presence of the homozygous recessive fan3fan3 gene pair in an otherwise conventional soybean plant in addition to reducing the linolenic acid content of the endogenously formed vegetable oil of the seeds has tended to decrease the concentration of the palmitic acid (C16:0) component of the vegetable oil, to increase the concentration of the stearic acid (C18:0) component of the vegetable oil, to increase the concentration of the oleic acid (C 18:1) component of the vegetable oil, and to decrease the concentration of the linoleic acid (C18:2) component of the vegetable oil based on the total fatty acid content.

It has been found that when the fan3fan3 gene pair is combined in a single soybean plant with the previously reported homozygous recessive gene pairs (1) fan1fan1 or fan1(A5)fan1(A5), and (2) fan2fan2 for the expression of reduced linolenic acid content, the expression of such gene pairs in combination is additive in nature and results in the expression of an endogenous linolenic acid content that commonly is less than that which previously has been reported in soybean seeds. The resulting linolenic acid concentration of the vegetable oil accordingly is less than that of any one of the source plants that initially provided the three recessive gene pairs or a combination of two of these gene pairs. In a preferred embodiment gene pair (1) is fan1(A5)fan1(A5).

When the homozygous recessive gene pairs (1) fan1fan1 or fan1(A5)fan1(A5), (2) fan2fan2, and (3) fan3fan3 are combined in a soybean plant and are grown under conventional field growing conditions, the linolenic acid concentration in the resulting vegetable oil commonly is less than 1.3 percent by weight (e.g., approximately 0.7 to less than 1.3 percent by weight), and preferably is no more than 1.1 percent by weight (e.g., approximately 0.7 to no more than 1.1 percent by weight) based on the total fatty acid content. Such vegetable oil additionally commonly contains approximately 9 to 11 percent by weight palmitic acid (C16:0), approximately 3.5 to 5.5 percent by weight stearic acid (C18:0), approximately 28 to 35 percent by weight oleic acid (C18:1), and approximately 50 to 56 percent by weight linoleic acid (C18:2) based upon the total fatty acid content.

The fan1fan1 gene pair was developed at Purdue University and is present in a moderately low linolenic acid mutant soybean line designated C1640. See, *J. Am. Oil Chem. Soc.,* 61:95 (1984). The C1640 line commonly exhibits a linolenic acid content of approximately 3.4 percent by weight based upon the total fatty acid content. Seeds of C1640 are publicly available from James R. Wilcox, Department of Agronomy, Lilly Hall, Purdue University, Lafayette, Ind. 47907, U.S.A. Additionally, 2,500 seeds of C1640 were deposited on Dec. 5, 1995 under the terms of the Budapest Treaty in the American Type Culture Collection (ATCC) at 12301 Parklawn Drive, Rockville, Md. 20852, U.S.A., and have been assigned Accession No. 97368.

The fan1(A5)fan1(A5) gene pair is believed to be at the same locus as the fan1fan1 gene pair, and is present in a mutant soybean line identified as A5 in commonly assigned U.S. Pat. No. 5,534,425. Applicants developed A5 in 1983 and found it to exhibit a linolenic acid concentration in the vegetable oil of approximately 2.9 to 4.1 percent by weight depending upon the environment. More specifically, the mutant line A5 formed an average linolenic acid concentration of 4.1 percent by weight in an Iowa U.S.A. planting, and an average of 2.9 percent by weight in two Puerto Rican plantings. In a series of plantings involving five states of the United States, the average linolenic acid concentration for A5 was 3.8 percent by weight. This line was selected from the progeny of soybeans mutagenized with ethyl methane sulfonate (EMS) as reported in *Crop Science* 23:192 (1983). The seed of A5 (Reg. No. GP44) is publicly available and has been distributed by the Committee for Agricultural Development, Iowa State University, Ames, Iowa 50011, since 1983. Additionally, 2,500 seeds of A5 were deposited on Dec. 5, 1995 under the terms of the Budapest Treaty in the American Type Culture Collection (ATCC) at 12301 Parklawn Drive, Rockville, Md., 20852, U.S.A., and have been assigned ATCC Accession No. 97371.

The fan2fan2 gene pair is present in soybean mutant FA47437EMS which was created through the treatment of parent soybean strain FA47437 with ethyl methane sulfonate (EMS) as described in commonly assigned U.S. Pat. No. 5,534,425. The FA47437EMS line commonly forms an average linolenic acid concentration of approximately 5.7 percent by weight. Seeds of FA47437EMS have been deposited under the terms of the Budapest Treaty in the American Type Culture Collection at 12301 Parklawn Drive, Rockville, Md. 20852, U.S.A. More specifically, 625 seeds of FA47437EMS were deposited on Jan. 10, 1989 and have been assigned ATCC Accession No. 40537. An additional 925 seeds of FA47437EMS were deposited on Dec. 19, 1995, and 1,575 seeds of FA47437EMS were supplementally deposited on Apr. 22, 1996. FA47437EMS sometimes is designated A23.

As described in U.S. Pat. No. 5,534,425, soybean A5 has been crossed with soybean FA47437EMS to obtain progeny that contain both the fan1(A5)fan1(A5) gene pair and the fan2fan2 gene pair. For instance, both of these gene pairs are present in publicly available soybeans designated 9253, A16, and A17. As previously indicated 9253 is described in commonly assigned U.S. Pat. No. 5,530,183, and exhibits a reduced linolenic acid content of approximately 2.5 to 3.5 percent by weight. A deposit of 2,500 seeds of 9253 has been made under the terms of the Budapest Treaty on Jan. 16, 1996 in the American Type Culture Collection (ATCC) and has received ATCC Accession No. 97415. A16 is discussed in commonly assigned U.S. Pat. No. 5,534,425. A17 is discussed in commonly assigned U.S. Pat. Nos. 5,534,425 and 5,557,037. Deposits of seeds of A16 and A17 have been made under the terms of the Budapest Treaty in the American Type Culture Collection and have received ATCC Accession Nos. 40538 and 40539 respectively. 625 seeds of A16 were deposited on Jan. 10, 1989. A16 forms the subject matter of commonly assigned Ser. No. 08/656,017, filed May 24, 1996(now U.S. Pat. No. 5,710,369), that is herein incorporated by reference. 625 seeds of A17 were deposited on Jan. 10, 1989, an additional 1,175 on Dec. 19, 1995, and 1,325 seeds of A17 were supplementally deposited on Apr. 22, 1996. A17 forms the subject matter of commonly assigned Ser. No. 08/656,016, filed May 24, 1996(now U.S. Pat. No. 5,714,669), that is herein incorporated by reference.

The presence of the homozygous recessive gene pairs fan1fan1, fan1(A5)fan(A5), and fan2fan2 can be confirmed by crossing to a plant that is a recognized source for such gene pairs and observing the phenotype of the offspring with respect to linolenic acid production in subsequent generations in a manner directly analogous to previously described with respect to fan3fan3. The gene pairs (1), (2), and (3) described herein in each instance are present at different gene loci. Such gene pairs individually or in combination can be readily transferred to other soybean germplasm in a straightforward manner by conventional plant breeding followed by selection. Accordingly, the requisite gene pair (i.e., fan3fan3) or gene pairs (i.e., fan1fan1 or fan1(A5)fan1(A5), fan2fan2, and fan3fan3) can be provided in descendants of the original plants formed through simple self-pollination or through cross-pollination (e.g., by backcrossing) with other soybean lines and cultivars followed by selection of the desired segregants.

The endogenously formed vegetable oil of the present invention can be derived or removed from the resulting soybean seeds by conventional means, such as by simple crushing and preferably by crushing as well as extraction (e.g., with hexane).

The soybean vegetable oil of the present invention in view of the reduced linolenic acid content is particularly suited for use in industrial and food applications where improved flavor stability is sought. For instance, when the oil is endogenously formed while under the influence of the combined presence of the three homozygous recessive gene pairs, the level of linolenic acid can be sufficiently reduced to extend the shelf-life of products in which it is incorporated and to perform better as a heat-transfer medium in applications such as cooking or frying. In some applications hydrogenation to increase stability is rendered unnecessary, and this obviates the formation of trans-fatty acids which some consumers prefer to minimize in the diet.

Fatty acid concentrations discussed herein except as otherwise noted were determined through the use of gas liquid chromatography as described by E. G. Hammond in "Organization of Rapid Analysis of Lipids in Many Individual Plants", Pages 321 to 330 (1991) appearing in H. F. Liskins and J. F. Jackson (ed.) "Essential Oils and Waxes. Modern Methods of Plant Analysis", Vol. 12, Springer-Verlag, Berlin. All percentages are by weight and are based upon the total fatty acid content of the oil removed from the seeds. Prior to the analysis, the vegetable oil was obtained by crushing the seed in a hydraulic press at $3.4 \times 10^6$ Pa, and was further extracted with distilled hexane. During such determination the glycerol esters present in the vegetable oil were converted to methyl esters by the use of sodium methoxide in methanol, and the methyl esters were separated and were quantified by gas liquid chromatography to provide the fatty acid concentrations that are specified. In accordance with the customary practice of the industry when expressing fatty acid percentages, no adjustment is made for the presence of the fatty acids as methyl esters or for the absence of glycerol to which fatty acids are attached in the endogenous oil.

The following Examples are presented as specific illustrations of the claimed invention. It should be understood however that the invention is not limited to the specific details set forth in the Examples.

EXAMPLE I

Seeds of an experimental soybean line designated A89-144003 were selected for mutagenesis. A representative sample of soybean line A89-144003 that had not undergone mutagenesis was found to exhibit the fatty acid profile reported in the following Table A when analyzed by liquid gas chromatography:

TABLE A

| Fatty Acid | Number of Carbon Atoms Per Molecule | Number of Double Bonds Per Molecule | Weight Percent |
|---|---|---|---|
| Palmitic | 16 | 0 | 12.0 |
| Stearic | 18 | 0 | 4.6 |
| Oleic | 18 | 1 | 16.8 |
| Linoleic | 18 | 2 | 57.5 |
| Linolenic | 18 | 3 | 9.1 |

Soybean line A89-144003 was developed as a selection from the cross of BSR 101×A1937, and possessed a high seed yield and moderate resistance to brown stem rot disease. Other soybean lines or cultivars could be similarly selected to undergo mutagenesis.

A representative sample of 2,500 mature seeds of the A89-144003 line was soaked in 2.5 liters of distilled water at room temperature for 8 hours with aeration, and the water was drained from the seeds. The seeds were next soaked for 9 hours at room temperature in 2.5 liters of an aqueous 0.1M. phosphate buffer containing a 0.025M. solution of ethyl methane sulfonate (EMS). The solution was drained from the seeds and the seeds were rinsed twice with distilled water. The wet seeds were next immediately planted in the field at Ames, Iowa, U.S.A. The plants resulting from the germination of such seeds were considered to be the M1 generation. The seeds formed following self-pollination were designated A89-144003EMS. The resulting seeds were planted in a progeny row in Puerto Rico to produce M2 plants that were harvested and threshed individually from each row. A five-seed bulk sample of seeds formed by self-pollination on each M2 plant was analyzed by gas liquid chromatography to determine the fatty acid concentrations of the components of the endogenously formed vegetable oil.

An M2 plant designated A89-144003EMS-81 was selected in view of the markedly reduced linolenic acid content of the vegetable oil. More specifically, A89-144003EMS-81 of the M2 generation was found to exhibit the fatty acid profile reported in the following Table B:

TABLE B

| Fatty Acid | Number of Carbon Atoms Per Molecule | Number of Double Bonds Per Molecule | Weight Percent |
|---|---|---|---|
| Palmitic | 16 | 0 | 10.9 |
| Stearic | 18 | 0 | 7.9 |
| Oleic | 18 | 1 | 49.5 |
| Linoleic | 18 | 2 | 27.2 |
| Linolenic | 18 | 3 | 4.4 |

Accordingly, the level of linolenic acid in the endogenously formed vegetable oil 10 was reduced by approximately 4.7 percent by weight following mutagenesis. In the M4 seeds formed on M3 plants grown in Puerto Rico a further selection from A89-144003EMS-81 that initially was designated 94FA73 was found to exhibit a further reduced linolenic acid content as reported in Table C that follows:

TABLE C

| Fatty Acid | Number of Carbon Atoms Per Molecule | Number of Double Bonds Per Molecule | Weight Percent |
| --- | --- | --- | --- |
| Palmitic | 16 | 0 | 9.7 |
| Stearic | 18 | 0 | 6.8 |
| Oleic | 18 | 1 | 54.2 |
| Linoleic | 18 | 2 | 25.6 |
| Linolenic | 18 | 3 | 3.8 |

In a subsequent generation following self-pollination seeds were produced at Ames, Iowa, U.S.A., and have been designated A26. The exhibited fatty acid profile is reported in Table D that follows.

TABLE D

| Fatty Acid | Number of Carbon Atoms Per Molecule | Number of Double Bonds Per Molecule | Weight Percent |
| --- | --- | --- | --- |
| Palmitic | 16 | 0 | 9.5 |
| Stearic | 18 | 0 | 5.6 |
| Oleic | 18 | 1 | 32.6 |
| Linoleic | 18 | 2 | 46.0 |
| Linolenic | 18 | 3 | 6.3 |

It will be noted that the linolenic acid concentration increased somewhat over that reported for Puerto Rico in view of the cooler temperatures encountered at Ames, Iowa, U.S.A. Such A26 nevertheless was found to exhibit a reduced linolenic acid concentration that was under the control of a novel homozygous recessive gene pair designated fan3fan3. Such gene pair has been shown through inheritance studies to be independent from and present at a different locus than previously reported gene pairs that exhibit a reduced linolenic acid content, such as fan1fan1, fan1(A5)fan1(A5), and fan2fan2. 2,500 seeds of A26 produced at Ames, Iowa, U.S.A., in the field as reported in Table D were deposited on December 2, 1996 under the terms of the Budapest Treaty in the American Type Culture Collection (ATCC) at 12301 Parklawn Drive, Rockville, Md. 20852, U.S.A., and have been assigned ATCC Accession No. 97812. Seeds of such deposit will be irrevocably made available upon the grant of a patent that makes reference to such deposit. Such fan3fan3 gene pair has been demonstrated to be readily transferable to other soybean germplasms through the use of conventional plant breeding techniques.

EXAMPLE II

Seeds of an experimental soybean line designated AX5711C04 were selected as a source of the homozygous recessive gene pairs fan1(A5)fan1(A5) and fan2fan2. Such gene pairs present in AX571 1C04 are believed to be identical to those present in soybeans 9253, A16 and A17 as previously discussed. AX5711C04, which has A16 in its ancestry, was obtained at Iowa State University from A16 by selection from the cross S23-12 ×AX5629, and possessed a higher yield than A16 coupled with the reduced linolenic acid content in the vegetable oil. When grown near Ames, Iowa, U.S.A., AX5711C04 exhibited a mean linolenic acid content of approximately 2.5 percent by weight in view of the expression of the expression of the fan1(A5)fan1(A5) and fan2fan2 gene pairs.

A26 containing the homozygous recessive fan3fan3 gene pair was crossed near Ames, Iowa, U.S.A. with AX5711C04 containing the homozygous recessive fan1(A5)fan1(A5) and fan2fan2 gene pairs. The resulting $F_1$ plants were harvested and were threshed individually and the resulting $F_2$ seeds were analyzed for fatty acid content by gas liquid chromatography. Each seed was carefully split into two parts prior to such analysis. The analysis was conducted on a single half-seed and the other half-seed was retained for planting when warranted by the fatty acid values that were obtained. Five of the $F_2$ seeds resulting from the cross were found to exhibit reduced linolenic acid contents of 1.57, 1.57, 1.59, 1.75, and 1.77 percent by weight based upon the total fatty acid content. The remaining half-seeds were germinated on paper towels and the resulting seedlings were transplanted to the field near Ames, Iowa, U.S.A. Five $F_2$ plants were grown, self-pollinated, and were individually harvested and were threshed.

The progeny of four of these plants in a subsequent generation following the cross were found to exhibit linolenic acid contents of 1.14, 1.17, 1.23, and 1.31 percent by weight based upon the total fatty acid content also when grown near Ames, Iowa, U.S.A. When further seeds from the same plants were analyzed, the lowest linolenic acid contents were found to be 0.73, 0.95, 0.98, and 1.00 percent by weight based upon the total fatty acid content.

The plant with the lowest linolenic acid content has been designated A29 and it has been confirmed to continue to yield the lowest linolenic acid content when grown both at Ames, Iowa, U.S.A., and at Puerto Rico. Such A29 soybean contains the homozygous recessive gene pairs fan1(A5)fan1 (A5), fan2fan2, and fan3fan3 in combination. 2,500 seeds of A29 produced in the field in a subsequent generation at Ames, Iowa, U.S.A., were deposited on Dec. 2, 1996 under the terms of the Budapest Treaty in the American Type Culture Collection (ATCC) at 12301 Parklawn Drive, Rockville, Md. 20852, U.S.A., and have been assigned ATCC Accession No. 97813. Seeds from such deposit will be irrevocably made available upon the grant of a patent that makes reference to such deposit. However, the availability of seeds of A26 and A29 is not to be construed as a license to practice the claimed invention in contravention of rights granted under the authority of any government in accordance with its patent or breeder's rights laws.

A fatty acid profile typically exhibited by A29 is reported in Table E that follows:

TABLE E

| Fatty Acid | Number of Carbon Atoms Per Molecule | Number of Double Bonds Per Molecule | Weight Percent |
| --- | --- | --- | --- |
| Palmitic | 16 | 0 | 9.5 |
| Stearic | 18 | 0 | 5.1 |
| Oleic | 18 | 1 | 33.8 |
| Linoleic | 18 | 2 | 50.6 |
| Linolenic | 18 | 3 | 1.1 |

As previously indicated the homozygous recessive gene pairs can be readily transferred to other soybean germplasms where they can similarly express the highly advantageous reduced linolenic acid content.

Although the invention has been described with reference to preferred embodiments, it is to be understood that variations and modifications may be resorted to as will be apparent to those skilled in the art. Such variations and modifications are to be considered within the purview and scope of the claims appended hereto.

We claim:

1. A soybean seed possessing the homozygous recessive gene pair fan3fan3 that is present in A26 having ATCC Accession No. 97812 for the expression of a reduced linolenic acid content in the endogenously formed vegetable oil of said seed.

2. A soybean seed designated A26 having ATCC Accession No. 97812 possessing the homozygous recessive gene pair fan3fan3 for the expression of a reduced linolenic acid content in the endogenously formed vegetable oil of said seed, or a soybean seed descended therefrom that possesses said homozygous recessive gene pair.

3. A soybean plant possessing the homozygous recessive gene pair fan3fan3 that is present in A26 having ATCC Accession No. 97812 for the expression of a reduced linolenic acid content in the endogenously formed vegetable oil in seeds formed thereon following self-pollination.

4. A soybean plant designated A26 having ATCC Accession No. 97812 capable of forming seeds upon self-pollination and possessing the homozygous recessive gene pair fan3fan3 for the expression of a reduced linolenic acid content in the endogenously formed vegetable oil of said seeds, or a soybean plant descended therefrom that possesses said homozygous recessive gene pair.

* * * * *

UNITED STATES PATENT AND TRADEMARK OFFICE
CERTIFICATE OF CORRECTION

PATENT NO.   : 5,850,030
DATED        : December 15, 1998
INVENTOR(S)  : Walter R. Fehr and Earl G. Hammond It is certified that error appears in the above-indentified patent and that said Letters Patent is hereby corrected as shown below:

On the title page, Item [54], insert

--This invention was made with government support under Project No. 3107 awarded by the United States Department of Agriculture. The government has certain rights in the invention.--

Signed and Sealed this

Eighth Day of June, 1999

Attest:

Q. TODD DICKINSON

Attesting Officer

Acting Commissioner of Patents and Trademarks